US010278622B2

(12) United States Patent
Arko et al.

(10) Patent No.: US 10,278,622 B2
(45) Date of Patent: May 7, 2019

(54) DEVICE FOR NON-INVASIVE MEASUREMENT OF BLOOD SUGAR LEVEL

(71) Applicant: DIA-VIT LTD, London (GB)

(72) Inventors: Zoran Arko, Ljubljana (SI); Tadej Tofant, Ptuj (SI)

(73) Assignee: DIA-VIT LTD. (GB)

( * ) Notice: Subject to any disclaimer, the term of this patent is extended or adjusted under 35 U.S.C. 154(b) by 0 days.

(21) Appl. No.: 15/764,016

(22) PCT Filed: Oct. 5, 2015

(86) PCT No.: PCT/IB2015/001788
§ 371 (c)(1),
(2) Date: Mar. 28, 2018

(87) PCT Pub. No.: WO2017/060746
PCT Pub. Date: Apr. 13, 2017

(65) Prior Publication Data
US 2018/0317821 A1    Nov. 8, 2018

(51) Int. Cl.
*A61B 5/1455*    (2006.01)
*A61B 5/145*    (2006.01)
*A61B 5/00*    (2006.01)

(52) U.S. Cl.
CPC ........ *A61B 5/14532* (2013.01); *A61B 5/1455* (2013.01); *A61B 5/0064* (2013.01);
(Continued)

(58) Field of Classification Search
None
See application file for complete search history.

(56) References Cited

U.S. PATENT DOCUMENTS 9,078,606 B1    7/2015  Bharj
2009/0163968 A1    6/2009  Donofrio
(Continued)

FOREIGN PATENT DOCUMENTS

EP    0880936 A2    12/1998
EP    1447658 A1    8/2004
(Continued)

OTHER PUBLICATIONS

David M. Nathan, et al., Translating the A1C Assay Into Estimated Average Glucose Values, Diabetes Care, Aug. 2008, vol. 31, No. 8, care.diabetesjournals.org.
(Continued)

*Primary Examiner* — Eric F Winakur
*Assistant Examiner* — Marjan Fardanesh
(74) *Attorney, Agent, or Firm* — The Watson IP Group, PLC; Jovan N. Jovanovic

(57)    ABSTRACT

The object of the invention is a device that allows measuring blood sugar levels in mammals—primarily humans—by measuring the refraction of electromagnetic radiation from the skin or body tissue, without the need for invasive sampling, such as penetrating or pricking the skin. The device uses the blue light portion of the visible spectrum and near-infrared (IR) radiation as a source of electromagnetic radiation. The device falls within the field of medical diagnostics and is essentially designed to be portable, so that the users can wear it on their wrists, for example. The signals of reflected light/radiation measured by the sensor unit are filtered by the frequency filtering set and mathematically processed in order to Calculate the current blood sugar level. The accuracy of the measurement result of the device is comparable to the results obtained with the standard method of measuring by blood sampling. A method for measuring of blood sugar level using said device is also disclosed.

15 Claims, 2 Drawing Sheets

Figure 1:
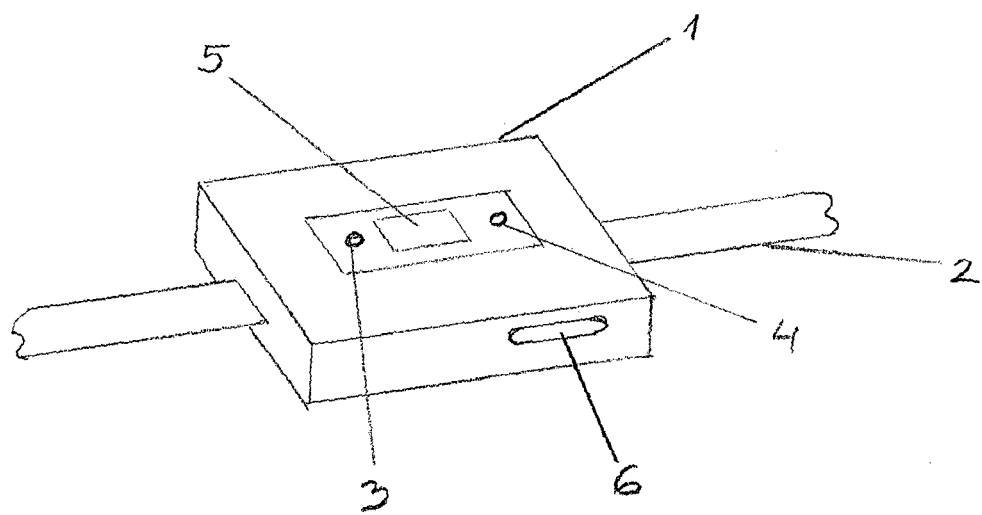

(52) U.S. Cl.
CPC .............. *A61B 5/0082* (2013.01); *A61B 5/681* (2013.01); *A61B 2562/0238* (2013.01)

(56) References Cited

U.S. PATENT DOCUMENTS

| | | |
|---|---|---|
| 2009/0316137 A1 | 12/2009 | Shioi |
| 2013/0075700 A1 | 3/2013 | Yang et al. |
| 2015/0112170 A1 | 4/2015 | Amerson, III |

FOREIGN PATENT DOCUMENTS

| | | |
|---|---|---|
| RU | 2506893 C1 | 2/2014 |
| WO | 9519562 A1 | 7/1995 |

OTHER PUBLICATIONS

Muhammad Sainal Abidin, et al., Measurement of Glucose in Blood Using a Simple Non Invasive Method, Materials Science Forum, 2015, pp. 105-109, vol. 827, Trans Tech Publications, Switzerland.

Yasuaki Hori, et al, Optical Glucose Monitoring Based on Femtosecond Two-Color Pulse Interferometry, Optical Review, 2006, 29-33, vol. 13 No. 1, Department of Mechanical Science and Bioengineering, Graduate School of Engineering Science, Osaka University, Toyonaka, Osaka 560-8531, Japan.

DEVICE FOR NON-INVASIVE MEASUREMENT OF BLOOD SUGAR LEVEL

The object of the invention is a device that allows measuring blood sugar levels in mammals—primarily humans—by measuring the refraction of electromagnetic radiation from the skin or body tissue, without the need for invasive sampling, such as penetrating or pricking the skin. The device uses the blue light portion of the Visible spectrum and near-infrared (IR) radiation as a source of electromagnetic radiation. The device operates within the field of medical diagnostics and is essentially designed to be portable, so that the users can wear it on their wrists, for example.

Information on blood sugar levels is especially important for diabetics. Diabetes (type I and II) is a potentially life-threatening disease, but by appropriately managing blood sugar levels it can be successfully controlled, so that a person with diabetes can live a full, normal, and active life. To successfully control diabetes, it is important to regulate blood sugar levels on a regular basis, which requires monitoring the BSL (blood sugar level) daily or even several times per day. Patients with complicated forms of diabetes determine the appropriate dosage of insulin on the basis of the BSL measured and depending on their intended nutritional regimen. Currently, most diabetes patients use the standard procedure for BSL control, which is invasive, as it usually involves obtaining a sample of blood by pricking, applying it to a test strip, and inserting the strip into the measuring device. Since for some patients it is necessary to monitor the BSL several times per day, such invasive procedure is unpleasant and painful. Therefore, various procedures have been developed to allow for non-invasive measurements of blood sugar levels.

Patent RU2506893 describes a device and procedure that employs ultrasonic waves of the frequencies from 100 Hz to 1500 Hz and from 7000 Hz to 10,000 Hz as an option for BSL measurement. The device does not use the visible light spectrum and is not portable.

U.S. Pat. No. 9,078,606B1 describes a device that uses micro-waves of several wavelengths. The device has a resonance chamber that receives micro-waves and oscillates the signal required. A finger is pressed onto the opening in the resonance chamber, so that an adequate quantity of tissue enters the chamber. This causes a change in oscillation frequency, which indicates the blood sugar level in the tissue. Depending on the specific frequency, the required signal is oscillated, and then used to calculate the BSL. The device allows measuring BSL only at the tip of the finger; moreover, it does not use the light of the visible spectrum.

Patent No. US2013075700 describes a device for measuring of multiple blood parameters using a variety of laser light sources, which are transferred to the measuring point via optical fibres. For is functionality the device requires a number of light and electrical filters, optical amplifiers, and processing units. It does not solve the issue of mobility, as it is too large and not portable for everyday use. The device uses an invisible light spectrum of 1400 nm to 2500 nm and higher wavelengths.

A solution allowing non-invasive measurements of blood sugar levels at the wrist is described in Patent Application No. US20150112170A1. The device uses a mid-infrared laser to detect the level of blood sugar. It transmits light emitted by the laser to the device via optical fibre, and, based on the reflection that the device receives the level of blood sugar is calculated. The device uses an invisible light spectrum above 1400 nm wavelength.

Patent Application No. PTCUS9500265 describes a device that performs non-invasive blood measurements by means of a light source in the invisible light spectrum. The device features several light sources, interconnected by a system of lenses, which amplify the light beam. The light beam is then focused on the sample, and a detector located below it detects the amount of light transmitted through the sample, calculating the concentration of various substances in the blood. The device measures the transmitted light, and not the reflected light; furthermore, it is not portable and is intended for use in hospitals.

A blue light source is also known to be used to measure the blood sugar level: in this case, the concentration of sugar in the blood is determined on the basis of light transmitted through a urine sample. Glucose in the sample absorbs the blue light, so the amount of transmitted light measured directly depends on the amount of glucose. The more glucose in the sample, the lower the result measured (Abidin M. S., Rajak A., Salam R. A., Munir M. M., Khairurrijal K. (2015) "Measurement of Glucose in Blood Using a Simple Non-Invasive Method", *Science Forum Materials*, Vol. 827, pp. 105-109).

Another known method is determining the average blood sugar level over time on the basis of glycated hemoglobin, in which case the amount of glycated hemoglobin is measured non-invasively by measuring the absorption of IR light. The amount of glucose in the blood is directly proportional to the measured quantity of glycated hemoglobin. This method does not allow to determine the current level of blood sugar (Nathan D. M., Kuenen J., Borg R., Zheng H., Schoenfeld D., Heine R. J. (2008). "Translating the A1C Assay into Estimated Average Glucose Values.". *Diabetes Care* 31 (8): 1473-8.).

So far, there are no available solutions for non-invasive blood sugar level measurements in mammals, primarily humans, using a combination of electromagnetic radiation of two wavelengths, i.e. visible spectrum light and IR radiation, where electromagnetic radiation that is reflected from the skin or body tissue is measured.

The technical problem solved by the invention is (1) determining a non-invasive method for blood sugar level measurement by using reflected light; the method has to be sufficiently accurate to replace the standard blood sampling method present on the market, which patients use to measure their blood sugar levels themselves; (2) and construction of a device for blood sugar level measurements employing this method, wherein the device is preferably portable. The signals of reflected light measured are used to calculate the current blood sugar level using appropriate filters and mathematical processing.

The invention is further described below and presented by embodiment and figures illustrating the device according to the invention and the process of measurement.

Figure 2:
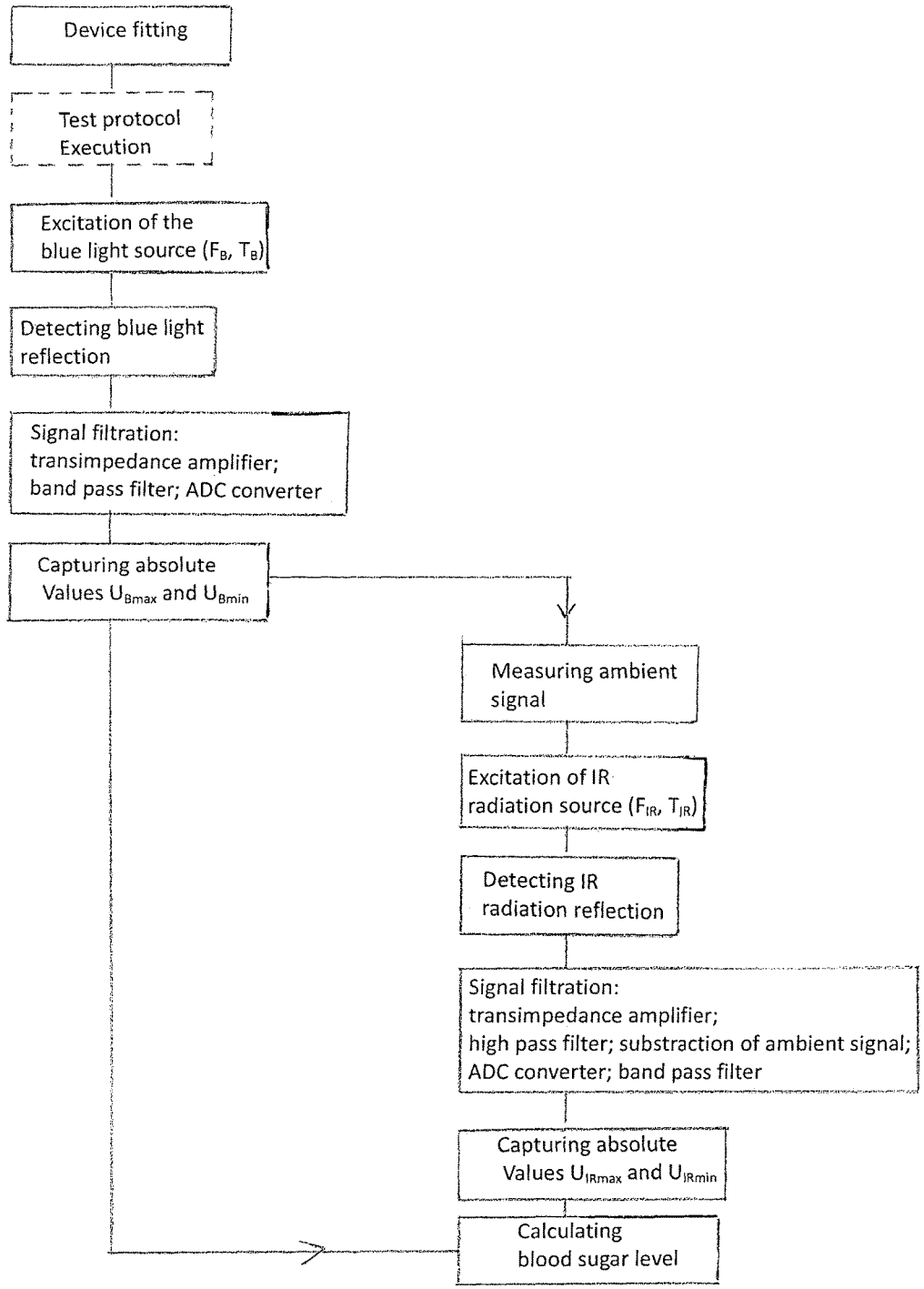

FIG. 1 represents one of the embodiments of the device according to the invention FIG. 2 represents the process of measurement according to one of the embodiments The device according to the invention includes:
- a blue light source with a wavelength of 430 to 480 nm, preferably 460 nm; in the presented embodiment this is a blue LED;
- an infrared (IR) radiation source with a wavelength of 700 to 3000 nm, preferably 940 nm; in the presented embodiment this is an IR LED;
- a sensor unit that measures the blue light and IR radiation reflected from the skin/tissue and converts it into a change in resistance or electrical current or voltage.

The sensor unit must have a sufficiently large range of wavelengths to convert the blue light and IR radiation. It is also possible to use two sensor units with a narrower range: that is, separate units for the blue light and the IR radiation. In the presented embodiment one sensor unit is used, namely a photodiode with a range of detected wavelengths from 300 to 1100 nm, which at the output creates current that is predominantly directly proportional to the intensity of light/radiation.

a frequency filtering set for filtering the signal coming from the sensor unit, wherein the filtration depends on whether detected reflected blue light or IR radiation is filtered. The frequency filtering set consists of one or more analog and/or digital frequency filters with which all frequencies of the signal are filtered out except for the frequency band around and including the frequency of blue light pulsation $F_B$, when measuring blue light, and the frequency band around and including the IR radiation pulsation frequency $F_{IR}$, when measuring IR radiation. Frequency filtration is required as the useful signal is initiated with a known frequency ($F_B$ and $F_{IR}$) and filtering is used to eliminate noise from the signal measured. In the presented embodiment "high pass" frequency filters, "band pass" filters and at least one ADC converter of at least 20 bit resolution for blue light and at least 10 bit resolution for IR radiation are used. The frequency filtering set can optionally include an amplifier, which appropriately amplifies the signal and/or changes the signal from current value to voltage value or vice versa before, during and/or after filtering. In the presented embodiment a transimpedance amplifier is used, which changes the current value to appropriate voltage value and amplifies the signal by a factor of 1:1000 when measuring blue light reflection and by a factor of 1:1 when measuring IR light reflection.

a processing unit with a memory for the program and a memory for storage and processing of measurement results that:
  a) controls the excitation of the blue light source with the pulsation frequency $F_B$ and the excitation time interval $T_B$. $F_B$ is selected from the frequency range between 100 and 300 kHz in different embodiments, preferably 200 kHz. $T_B$ is between 1 and 10 seconds in different embodiments, preferably 7 seconds;
  b) controls the excitation of the IR radiation source with the pulsation frequency $F_{IR}$ and the excitation time interval $T_{IR}$. $F_{IR}$ is selected from the frequency range between 1 kHz and 50 kHz in different embodiments, preferably 10 kHz. $T_{IR}$ is between 1 and 10 seconds in different embodiments, preferably 7 seconds;
  c) controls the filtering of the frequency filtering set;
  d) captures searched signal values from the filtered signal from individual measurement intervals for the blue light and separately for the IR radiation. The measurement interval is usually equal to the excitation interval, as is the case in the presented embodiment, but it may also be shorter, e.g. the start of the measurement interval can be delayed by up to 0.5 seconds, so that transitional phenomena are eliminated from the measurements. In one of the embodiments, the searched values are the absolute maximum voltage value and the absolute minimum voltage value at each measuring interval, namely $U_{Bmax}$ and $U_{Bmin}$ when measuring blue light reflection, and $U_{IRmax}$ and $U_{IRmin}$ when measuring IR radiation reflection.
  e) using a preset mathematical algorithm, it calculates the blood sugar level from the searched values.

The power supply of the device is provided by an electric battery or another source of electricity. Preferably, the device is powered via a power battery, located behind the display.

The blue light source, the IR radiation source, and the sensor unit are facing the skin/tissue during measuring and are in close contact with the skin/tissue. Preferably, the light/radiation source and the sensor unit are next to each other, with both sources as close as possible to the sensor unit. Light/radiation penetrates the skin and tissue, and part of the light/radiation is absorbed by the skin and tissue, whereas another part of the light/radiation reflects from the skin and tissue and reaches the sensor unit. The best measurement results are obtained if the sources and the sensor unit are placed on a part of the body with the least amount of adipose tissue, for example, on the wrist.

Optionally the device can include a display which shows the BSL values, guides the measuring process, notifies about errors, etc. The display is located on the upper side of the device, that is, the side that is not in contact with the skin. In the presented embodiment, the display is an OLED screen.

Furthermore, the device can optionally contain a communications circuit, for example, Bluetooth, which enables programming, controlling the device, and/or transmitting the measured values and calculated BSL to a PC or another device.

The device is protected by casing, which in the presented embodiment is made of plastic material. Both sources and the sensor unit are coated with a transparent silicone, permeable by visible light and infra-red radiation. The device is in close contact with the skin at the measuring location in order to avoid external influences, such as sunlight, on the execution of the measurements.

The device can optionally include a strap for mounting it on the measurement spot, preferably on the wrist. The strap is preferably implemented as a bracelet or a belt.

The device can optionally include one or more buttons for switching the device on/off and controlling the display settings. Such button or buttons can be implemented on a touch-screen.

The method of blood sugar level measuring with the device according to the invention includes the following steps.

The device is mounted on the measurement location so that the sources of light/radiation and the sensor unit are in close contact with the skin/tissue of the measurement location.

Optionally, prior to starting the measurement, a test protocol can be carried out, verifying that the device is properly mounted on the measurement location on the body, preferably, on the wrist. The first step of the test protocol is exciting either the light source or the IR radiation source with the selected pulsation frequency. The sensor unit detects light or radiation reflected from skin/tissue and emits a signal, which is filtered through the frequency filtering set, which filters out all frequencies except for a narrow frequency band around the selected frequency. The processor unit compares the signal obtained with the preset value. If the signal obtained is greater than the preset value, it means that the reflection is strong enough and the device is securely attached to the measurement location. Therefore, measurement process continues. If the signal obtained is lower than the preset value, in the embodiment, the display shows the appropriate warning, so that the user can fix the position of the device on the body.

Measurements using the blue light source follow. The blue light source is excited by pulsation with the frequency $F_B$ in the measuring interval $T_B$. The sensor unit detects the reflected light and converts it to an electrical signal: in the presented embodiment, electric current. The electrical signal in the presented embodiment is stored in the memory of the processing unit.

The electrical signal is then directed to the frequency filtering set, which filters out all the frequencies except for the specified frequency band around and including the frequency of blue light pulsation $F_B$ and optionally amplifies the signal before or after filtration.

In the presented embodiment, the pulsation frequency $F_B$ is equal to 200 kHz, and the measuring interval is equal to the excitation interval of the blue light source $T_B$, which is 7 seconds. In the presented embodiment an adequate filtration is carried out in such a way that the signal from the sensor unit is first amplified by the transimpedance amplifier with an amplifying factor of 1000, and at the same time the electrical signal, that is electrical current, is converted into voltage before performing the filtration. In the presented embodiment, amplifying the signal is necessary, as the values of the measured current are in the pA range, and processing the non-amplified signal is virtually impossible, since filtration would not be selective. Amplification increases the filtration selectivity of the measured signal. In the presented embodiment, filtration of the signal with "band pass" filtration follows, which filters out all the frequency components from the signal, with the exception of frequency component $F_B$ and the surrounding band ±10%. In the presented embodiment, $F_B$ is equal to 200 kHz. Conversion of the signal to digital format follows, performed by the ADC converter, which must have at least 20 bit resolution, so that the converted signal is sufficiently precise for further processing and measurement.

From the signal thus filtered, when measuring the reflected blue light, searched values of the signal are captured, used in the following steps to calculate the value of the blood sugar level.

In the presented embodiment, the searched values in measuring blue light reflection are the absolute maximum voltage $U_{Bmax}$ and the absolute minimum voltage $U_{Bmin}$, where the latter is the minimum voltage value that is greater than zero.

Measurements using the IR radiation source follow. The IR radiation source is excited by pulsation with the frequency $F_{IR}$ in the measuring interval $T_{IR}$. The sensor unit detects the reflected radiation and converts it to an electrical signal: in the presented embodiment, electric current. The electrical signal in the presented embodiment is stored in the memory of the processing unit.

The electrical signal is then directed to the frequency filtering set, which filters out all the frequencies except for the specified frequency band around and including the frequency of IR radiation pulsation frequency $F_{IR}$ and optionally amplifies the signal before or after filtration.

In the presented embodiment, the pulsation frequency $F_{IR}$ is equal to 10 kHz, and the measuring interval is equal to the excitation interval of the IR radiation source $T_{IR}$, which is 7 seconds. In the presented embodiment an adequate filtration is carried out so that the signal from the sensor unit, before performing the filtration, is directed to the transimpedance amplifier with an amplifying factor of 1, which converts the electrical signal, which is electrical current, into voltage.

Signal amplification in the case of the presented embodiment is not needed, since current values in the signal are already in the nA range. In the presented embodiment, filtration of the signal with the "high pass" frequency filter follows, which filters out all the frequencies under 20 kHz from the signal. From the signal thus filtered, the ambient component of the signal is subtracted. The ambient component of the signal represents any electromagnetic radiation detected by the sensor unit and not transmitted by the IR radiation source, such as light or heat in the room, the body heat, solar radiation, and the like. Therefore, this component represents the noise that need to be eliminated from the signal. Measuring the ambient component of the signal will be explained below. If the ambient component of the signal is greater than the total measured signal, which is the sum of the useful signal (the result of the IR radiation source of the device) and noise (including the ambient component of the signal), the measurement of the reflected IR radiation is repeated, since the signal to noise ratio is too high.

Measuring the ambient component of the signal can be performed before measuring the IR signal or after measuring the IR signal in the following manner: the device is properly mounted on the hand. At least half a second must pass between the last excitation of any light/radiation source and the measurement of the ambient component, so as to minimise the impact/thermal radiation from the previous measurements. During the measuring interval of the ambient component, the IR radiation or the blue light source must not be excited. This way, only the ambient or body electromagnetic radiation is actually measured, which represents the noise. The ambient component measurement interval is preferably in the range of 0.5 seconds to 0.7 seconds, but it does not need to be greater than 1 second. The signal thus obtained can be stored in the processing unit memory, in which case the signal is amplified by the transimpedance amplifier and converted from current into voltage with the same factor as the measured IR signal.

In the presented embodiment, conversion of the signal to digital format follows, and is performed by the ADC converter, which must have at least 10 bit resolution, preferably 16 bit. "Band pass" frequency filtration is performed for the digital signal with the main frequency component $F_{IR}$, which is 10 kHz, and the surrounding band ±10%.

From the signal thus filtered, when measuring the reflected IR radiation, searched values of the signal are captured, and used in the following steps to calculate the value of the blood sugar level. In the presented embodiment, the searched values in measuring IR radiation reflection are the absolute maximum voltage $U_{IRmax}$ and the absolute minimum voltage $U_{IRmin}$, where the latter is the minimum voltage value that is greater than zero.

The order in which the measurements of the reflected blue light and the reflected IR radiation are performed is not significant, since the measurements are independent; the IR radiation reflection can be measured first, and then the blue light reflection, or vice versa.

The next step is calculating of the blood sugar level value with a predefined mathematical algorithm using the searched values of both measurements. The searched values filtered out from the filtered signal can be measured as current or voltage, and, in addition to the maximum and minimum value, they contain other values, such as the average value in each measuring interval. Naturally, if selecting any other values than the ones set out in the presented embodiment, it is necessary to adjust the mathematical algorithm calculating the blood sugar level.

In the presented embodiment, $X_1$ and $X_2$ factors are calculated from $U_{Bmax}$, $U_{Bmin}$, $U_{IRmax}$, and $U_{IRmin}$.

The formula for calculating X1 is in the presented embodiment adapted using the known formula for calculating oxygen and indirectly hemoglobin by measuring the amount of red light and IR radiation ("Pulse Oximetry". Oximetry.org. 2002 Sep. 10). In the presented embodiment it is accordingly adjusted for measuring blood sugar level by measuring the reflected blue light and IR radiation.

$$X_1 = \frac{(U_{Bmax} - U_{Bmin}) \times U_{IRmin}}{(U_{IRmax} - U_{IRmin}) \times U_{Bmin}}$$

The formula for calculating $X_2$ is in the presented embodiment acquired empirically, wherein $X_2$ is directly proportional to the natural logarithm of the $U_{Bmax}$ to $U_{Bmin}$ ratio and reversely proportional to the natural logarithm of the $U_{IRmax}$ to $U_{IRmin}$ ratio.

$$X_2 = \frac{\ln\left(\frac{U_{Bmax}}{U_{Bmin}}\right)}{\ln\left(\frac{U_{IRmax}}{U_{IRmin}}\right)}$$

The AG blood sugar level value in the presented embodiment is calculated according to the empirical formula:

$$AG = K_1 \times \frac{X_1}{X_2} - K_2$$

The $K_1$ and $K_2$ constants reflect specific electronic elements that were used in the construction of the device, as well as the absorption factor of the particular type of skin. $K_1$ and $K_2$ can be determined empirically or calculated on the basis of the characteristics of specific electronic elements and the absorption factor of the particular skin type. In the presented embodiment, constants $K_1$ and $K_2$ are determined empirically in the following way: upon every measurement of blood sugar level using the device according to the presented embodiment, measurements were also carried out using the standard method of blood sampling. By comparison of the two measurements, constants $K_1$ and $K_2$ were determined so that there would be least deviations between the measurements. Thus, the empirically determined constants for the European (light) skin type are:

$K_1$=4.61

$K_2$=1.13

Optionally, a certain device can be calibrated for a specific skin type: the calibration procedure determines the absorption factor for the specific skin type on the basis of additional measurements of the IR radiation reflection and/or blue light reflection. Another option is to select the skin type from the preset values of $K_1$ and $K_2$ before measuring, in which case both constants for a specific skin type are stored in advance in the program on the processor unit that calculates the blood sugar level value.

In the presented embodiment, the obtained blood sugar level value is then displayed on the screen. In other embodiments the value obtained can be further processed, or the result can activate certain messages to be displayed to the user through preset logic, such as: within normal range; below the normal range, above the normal range.

The processor unit can optionally compare the result obtained to a preset range of expected values. In so far as the result obtained is within the preset range, measurements are accepted as successful and, in the presented embodiment, are displayed on the screen. In so far as the result obtained is not within the preset range, the measurement is discarded and, if necessary, repeated.

Measurements can be carried out repeatedly. The obtained results of successful measurements are statistically processed and transmitted, for example, as the average value of all successful measurements or as a value±error.

According to the method in the presented embodiment, measurements of blood sugar level in the range between 4 mmol/L and 13 mmol/L can be performed, with tolerance for an error in measurements up to 20%. There are multiple causes for an error, namely: device loosely fit on the skin, damaged skin or body hair altering the absorption factor, constricted blood vessels, etc.

EMBODIMENT

In one of the embodiments, shown in FIG. 1, the device according to the invention is composed of the casing 1 and mounting straps 2 for firm attachment to the wrist. On the side of the casing that is in contact with the skin on the wrist, a blue LED 3 is installed as the source of blue light, an IR LED 4 as the source of IR radiation, and a receiving photodiode 5 as the sensor unit. The blue LED emits light with a wavelength of 460 nm, the IR LED emits radiation with a wavelength of 940 nm, and the receiving photodiode has a range of detected wavelengths of 300 to 1100 nm with a maximum sensitivity of 920 nm. On the opposite side of the casing 1, the OLED screen is located, performing as a display, which is not shown on the figure. At the side of the casing, there is a multifunctional button 6 for switching the device on/off and controlling the display settings. The casing of the device is made of plastic material; both LEDs and the photodiode are coated with silicone, which is transparent and permeable by visible light and IR radiation.

The casing 1 contains all the electronic elements that are responsible for the operation of the device. The processor unit and the frequency filtering set are implemented with the Cypress PSOC 5 chip. Part of the frequency filtering set used for filtering the reflected blue light consists of a transimpedance amplifier with an amplifying factor of 1000, a "band pass" filter, and a 24-bit ADC converter. Amplifying the signal is necessary, as the values of the measured current at the photodiode are in the pA range, and further processing of the non-amplified signal would be virtually impossible, since filtration would not be appropriately selective. Signal amplification increases the filtration selectivity of the measured signal.

The frequency filtering set for filtering the reflected IR radiation consists of a transimpedance amplifier with an amplifying factor of 1, a "high pass" filter, and a 16-bit ADC converter.

For communication with external devices, the casing contains a Bluetooth circuit of the 4th generation. The casing also contains lithium-polymer based batteries. The batteries are charged through two dock connectors, which can also serve to provide direct power supply to the device.

FIG. 2 shows a method according to one of the embodiments. The method involves fixing the device on the wrist, carrying out the test protocol, confirming that the device is properly mounted on the wrist. Blue light source excitation follows; it pulsates with the frequency $F_B$ in the measuring interval $T_B$. The sensor unit detects the reflected light and converts it into electric current. Signal filtration follows, where the signal from the sensor unit is first amplified by the transimpedance amplifier, followed by signal filtration with the "band pass" filter and signal conversion into digital form by the ADC converter. From thus filtered signal, when measuring the reflected blue light, searched values are captured, which are the absolute maximum voltage $U_{Bmax}$ and the absolute minimum voltage $U_{Bmin}$, where the latter is the minimum voltage value that is greater than zero. Ambient component measuring follows and then IR radiation source excitation: it pulsates with the frequency $F_{IR}$ in the measuring interval $T_{IR}$. The sensor unit detects the reflected radiation and converts it into electric current. Signal filtration follows, where the signal from the sensor unit is directed to the transimpedance amplifier, followed by signal filtration with the "high pass" filter. From the signal thus filtered the ambient component of the signal is subtracted. Conversion of the signal to digital format follows, performed by the ADC converter and digital signal filtration with the "band pass" filter. From thus filtered signal, when measuring the reflected IR radiation, searched values are captured, which are the absolute maximum voltage $U_{IRmax}$ and the absolute minimum voltage $U_{IRmin}$, where the latter is the minimum voltage value that is greater than zero. Calculating of the blood sugar level value follows, using a predefined mathematical algorithm using the searched values of both measurements.

The invention claimed is:

1. A device for non-invasive measurement of blood sugar levels in mammals, preferably humans, by measuring electromagnetic radiation that is reflected from the skin and/or tissue, characterised in that the device includes:
   a blue light source with a wavelength of 430 nm to 480 nm;
   an infrared (IR) radiation source with a wavelength of 700 nm to 3000 nm;
   a sensor unit for measuring a blue light and an IR radiation reflected from the skin and/or tissue and converting them into a change in resistance or electrical current or voltage;
   a frequency filtering set for signal filtering, comprising one or more analog and/or digital frequency filters with which all frequencies of the signal are filtered out except for a determined frequency band around and including a frequency of the blue light pulsation $F_B$, when measuring blue light, and a determined frequency band around and including an IR radiation pulsation frequency $F_{IR}$, when measuring IR radiation; and
   a processing unit with a memory for the program and a memory for storage and processing of measurement results that:
   a) controls the excitation of the blue light source with the pulsation frequency $F_B$ and the excitation time interval $T_B$, where $F_B$ is selected from the range between 100 kHz and 300 kHz, and $T_B$ is selected from the range between 1 second and 10 seconds;
   b) controls the excitation of the IR radiation source with the pulsation frequency $F_{IR}$ and the excitation time interval $T_{IR}$, where $F_{IR}$ is selected from the range between 1 kHz and 50 kHz, and $T_{IR}$ is selected from the range between 1 second and 10 seconds;
   c) controls the filtering of the frequency filtering set;
   d) from individual measuring intervals for the blue light and separately for the IR radiation captures searched signal values from the filtered signal, and
   e) from the searched signal values calculates the blood sugar level using a preset mathematical algorithm.

2. The device according to claim 1, characterized in that the blue light source is a blue LED with a wavelength of 460 nm, pulsating with the frequency $F_B$ equal to 200 kHz in the excitation time interval $T_B$ of 7 seconds, the source of IR radiation is an IR LED with a wavelength of 940 nm, pulsating with the frequency $F_{IR}$ of 10 kHz in the excitation time interval $T_{IR}$ of 7 s, the sensor unit is a photodiode with a range of detected wavelengths from 300 to 1100 nm, and the blue LED and IR LED are mounted on the device as close as possible to the photodiode.

3. The device according to claim 1, characterised in that the frequency filtering set includes "high pass" frequency filters, "band pass" frequency filters, and the ADC converter which has at least 20 bit resolution for blue light and at least 10 bit resolution for IR radiation.

4. The device according to claim 1, characterised in that the frequency filtering set additionally includes a transimpedance amplifier with an amplifying factor of 1:1000 when measuring blue light reflection and a transimpedance amplifier with an amplifying factor of 1:1 when measuring IR radiation reflection.

5. The device according to claim 1, characterised in that the device additionally includes a display for displaying the level of blood sugar, a communications circuit that enables programming and controlling the device and/or sending the measured and calculated values of blood sugar level to a computer or other device, and at least one button for turning the device on and off and controlling display settings.

6. The device according to claim 1, characterised in that the device includes a strap for fastening the device to the measurement spot on the body, preferably on the wrist, and a battery or other power source.

7. The device according to claim 1, characterised in that the searched signal values in the filtered signal are absolute maximum voltage values and absolute minimum voltage values at each measuring interval, namely $U_{Bmax}$ and $U_{Bmin}$ when measuring blue light reflection, and $U_{IRmax}$ and $U_{IRmin}$ when measuring IR radiation reflection.

8. A method for measuring a blood sugar level that includes the following steps:
   attaching the device of claim 1 to the measuring location on the body, so that the blue light source, the IR radiation source, and the sensor unit are in close contact with the skin and/or tissue of the measuring location;
   measuring with the blue light source, which includes:
   a) exciting the blue light source, so that it is pulsating with the frequency $F_B$ in the time interval $T_B$,
   b) detecting the reflected light with the sensor unit and converting the detected light into electrical signal,
   c) filtering the signal from the sensor unit with the frequency filtering set that filters out the signal of all frequencies except for the specified frequency band around and including the frequency of blue light pulsation $F_B$,
   d) capturing searched signal values from the filtered signal when measuring the blue light reflection;
   measuring with the IR radiation source, which includes:
   a) exciting the IR radiation source, so that it is pulsating with the frequency $F_{IR}$ in the time interval $T_{IR}$,
   b) detecting the reflected IR radiation with the sensor unit and converting the detected IR radiation into electrical signal,
   c) filtering the signal from the sensor unit with the frequency filtering set that filters out the signal of all frequencies except for the specified frequency band around and including the frequency of blue light pulsation $F_{IR}$, d) capturing searched signal values from the filtered signal when measuring the IR radiation reflection;

calculating the value of blood sugar level with a predefined mathematical algorithm using the searched signal values of blue light reflection measurements and the searched signal values of the IR radiation reflection measurements, wherein measuring with the blue light source and measuring with the IR radiation source are mutually independent, so the order is arbitrary.

9. The method according to claim 8, characterised in that the searched signal values in the filtered signal are absolute maximum voltage values and absolute minimum voltage values at each measuring interval, namely $U_{Bmax}$ and $U_{Bmin}$ when measuring blue light reflection, and $U_{IRmax}$ and $U_{IRmin}$ when measuring IR radiation reflection.

10. The method according to claim 8, characterised in that the signal filtration when measuring with the blue light source includes:

a. signal amplification with a transimpedance amplifier with an amplifying factor of 1000, and at the same time an electrical signal, that is electrical current, is converted into voltage, b. followed by signal filtration with "band pass" filtration, which filters out all the frequency components from the signal, with the exception of frequency component $F_B$, equal to 200 kHz and the surrounding band ±10%, and c. conversion of the signal to digital format by the ADC converter, which has at least 20 bit resolution.

11. The method according to claim 8, characterised in that the signal filtration when measuring with the IR radiation source includes:

a. directing the signal from the sensor unit to the transimpedance amplifier with an amplifying factor of 1:1, where the electrical signal, that is electrical current, is converted into voltage, b. signal filtering with the "high pass" frequency filter, which filters out all the frequencies under 20 kHz from the signal, c. deducting an ambient component from the thus filtered signal, d. conversion of the signal to digital format by the ADC converter, which has at least 10 bit resolution, and e. frequency filtration with "band pass" filtration, which filters out all the frequency components from the signal, with the exception of frequency component $F_{IR}$, equal to 10 kHz, and the surrounding band ±10%.

12. The method according to claim 11, characterised in that the ambient component measuring is performed before measuring the IR signal or after measuring the IR signal, wherein at least half a second must pass between the last excitation of any light/radiation source and measuring the ambient component and during measuring the IR radiation source and the blue light source must not be excited; thus obtained signal is amplified through the transimpedance amplifier and converted from current to voltage with the same factor as the IR signal measured.

13. The method according to claim 9, characterised in that the value of blood sugar level is calculated by the following formula:

$$AG = K_1 \times \frac{X_1}{X_2} - K_2$$

where $$X_1 = \frac{(U_{Bmax} - U_{Bmin}) \times U_{IRmin}}{(U_{IRmax} - U_{IRmin}) \times U_{Bmin}}$$

and $$X_2 = \frac{\ln\left(\frac{U_{Bmax}}{U_{Bmin}}\right)}{\ln\left(\frac{U_{IRmax}}{U_{IRmin}}\right)}.$$

14. The method according to claim 9, characterised in that prior to starting the measurement, a test protocol is carried out, verifying that the device is properly mounted on the measurement location on the body, in which either the blue light source with the pulsation frequency $F_B$ or the IR radiation source with the pulsation frequency $F_{IR}$ is excited, the sensor unit detects blue light or IR radiation reflected from the skin and/or tissue, converts it to a signal that is filtered through the frequency filtering set; the processor unit compares the filtered signal with a preset value and if the signal obtained is greater than the preset value, it means that the reflection is strong enough, therefore, the device is properly attached to the body part.

15. The method according to claim 9, characterised in that the measurement method is repeated several times in a row, wherein so obtained successful measurement results are statistically processed and provided to the user as the average value of all measurements or as value±error.

* * * * *